United States Patent [19]

Bernardi

[11] Patent Number: 5,176,632
[45] Date of Patent: Jan. 5, 1993

[54] WEARABLE ARTIFICIAL PANCREAS

[75] Inventor: Luigi Bernardi, Rome, Italy

[73] Assignee: Ampliscientifica S.R.L., Milan, Italy

[21] Appl. No.: 527,129

[22] Filed: May 22, 1990

[30] Foreign Application Priority Data

May 29, 1989 [IT] Italy .............................. 48005 A/89

[51] Int. Cl.⁵ ............................................ A61M 31/00
[52] U.S. Cl. ..................................... 604/66; 604/65; 128/635
[58] Field of Search .................... 128/632, 635; 604/4, 604/5, 27, 28, 50-52., 65-67

[56] References Cited

U.S. PATENT DOCUMENTS

| | | | |
|---|---|---|---|
| 3,512,517 | 5/1970 | Kadish et al. | 604/27 |
| 4,240,438 | 12/1980 | Updike et al. | 128/635 |
| 4,245,634 | 1/1981 | Albisser et al. | 128/635 |
| 4,253,456 | 3/1981 | Schindler et al. | 604/5 |
| 4,458,686 | 7/1984 | Clark, Jr. | 128/635 |
| 4,467,811 | 8/1984 | Clark, Jr. | 128/635 |
| 4,515,584 | 5/1985 | Abe et al. | 604/66 |
| 4,526,569 | 7/1985 | Bernardi | 604/65 |
| 4,633,878 | 1/1987 | Bombardieri | 128/635 |
| 4,671,288 | 6/1987 | Gough | 128/635 |
| 4,680,268 | 7/1987 | Clark, Jr. | 128/635 |
| 4,711,245 | 12/1987 | Higgins et al. | 128/635 |
| 4,721,677 | 1/1988 | Clark, Jr. | 128/635 |
| 4,726,381 | 2/1988 | Jones | 128/632 |
| 4,830,011 | 5/1989 | Lim | 128/635 |
| 4,854,322 | 8/1989 | Ash et al. | 128/635 |
| 4,953,552 | 9/1990 | DeMarzo | 128/635 |
| 5,002,661 | 3/1991 | Chick et al. | 604/4 |

FOREIGN PATENT DOCUMENTS 0134758 4/1984 European Pat. Off. .
0206531 5/1986 European Pat. Off. .

OTHER PUBLICATIONS

Rigaud et al. "Manual L⁻ Lactate Analyzer" 9th Annual Conference of the IEEE Engineering in Med. & Biology, 1987.

Primary Examiner—Stephen C. Pellegrino
Assistant Examiner—Michael Rofa
Attorney, Agent, or Firm—Bucknam and Archer

[57] ABSTRACT

A device for the continuous quantitative determination of glucose in the blood of a diabetic patient over a period of 24-36 hours, comprises a container for a saline solution with heparin, a microdialyzing needle inserted into a vein of a diabetic patient, a pump for injecting the solution into the microdialyzing needle, a semipermeable hollow fiber membrane located externally of the needle whereby dialysis occurs between the blood and the solution and only glucose and other substances of low molecular weight below 100,000 daltons go through the membrane and the concentration of the glucose and other substances of low molecular weight below 100,000 daltons inside the needle is proportional to that of the external side of the membrane. The needle is provided with an outgoing conduit, the conduit leads to a sensor, which comprises an enzymatic membrane coupled with a Platinum-Silver electrode. The glucose goes into the conduit, oxidation of glucose to gluconic acid and hydrogen peroxide occurs and the hydrogen peroxide is decomposed to give $H_2O$ and oxygen with the liberation of two electrons whereby electric current is produced and the concentration of glucose in the blood is determined by determining the amount of current produced.

8 Claims, 5 Drawing Sheets

WEARABLE ARTIFICIAL PANCREAS

The present invention relates to extracorporeal devices to be worn by an individual for the continuous quantitative determination over a period of 24-36 hours of low molecular weight substances below 100.000 daltons, the concentration of which varies continuously in the human body, without removing the blood from the individual. More specifically, the present invention relates to the continuous quantitative determination of substances such as glucose in the case of diabetic people. It could also be applied to the determination of lactate in athletes or in people with heart diseases, without removing blood from the body, while allowing the individual to carry on his normal activities. Further, the device in the case of diabetic people may act as a wearable artificial extracorporeal endocrine pancreas because it may also provide for the injection of insulin depending upon the measurements obtained.

BACKGROUND OF THE INVENTION

The first artificial endocrine pancreas has been marketed by Miles Laboratories, Elkart, Ind. under the trademark BIOSTATOR. The device consists of a double lumen catheter for the continuous drawing of blood samples, used for blood glucose determinations and of a pump for infusing insulin and/or glucose into the examined patient. This device requires the removal of about 50 cc of blood which are wasted after the measurements. The apparatus is of large dimensions, and the individual must be confined to his bed. Further, the measurements are not satisfactorily accurate.

The device, Betalike, manifactured by Esaote Biomedica. Genoa, Italy has provided some improvements because it utilizes small hollow fibers hemofilter for blood ultrafiltration. Hence the measurements are more accurate and blood is reinfused into the patient, the determinations being carried out on ultrafiltered liquid. It is also of smaller dimensions than the BIOSTATOR, but still it cannot be worn by the patient, which again must be confined to his bed.

Other similar devices have been proposed by Gambro. Lund, Sweden, which uses a dialysis cartridge instead of hemofiltration, and Nikkiso, Japan, in which apparatus blood drawing and glucose analysis is not continuous but intermittent.

All these devices are not wearable by the patient for their dimensions and weight. Further, they all need removal of blood from the patient for the analysis.

SUMMARY OF THE INVENTION

An object of the present invention is to provide an apparatus which is of small dimensions and which permits the quantitative determination of substances of low molecular weight in the blood over a period of 24-36 hours, without removing blood from the patient, while allowing the patient to continue his normal activities.

Another object is to provide a device which permits to inject substances, if required, into the human body, depending upon the measurements obtained, for instance, insulin or glucose, in the case of diabetic people.

Although the invention may have several applications, the invention will be described in detail with reference to the determination of glucose, the concentration of which varies continuously in the blood in diabetic people over a period of 24-36 hours.

The crux of the present invention resides in carrying out the dialysis in the body by means of a microdialyzing needle which is inserted into a vein of the patient. A semipermeable hollow fiber membrane surrounds the terminal part of the needle. Substances of low molecular weight, particularly glucose, go through the membrane, while the higher molecular weight substances, such as fibrin; and cells do not go through. Further, a solution containing heparin is introduced into the needle in order to prevent blood clotting in the proximity of its terminal part. The liquid flows into the space between the needle and the hollow fiber membrane. Proportional equilibrium is reached between the solution being introduced through the needle and the blood which flows outside the membrane. The solution then flows to an enzymatic-amperometric sensor used to determine quantitatively the amount of glucose.

BRIEF DESCRIPTION OF THE DRAWINGS

The invention is illustrated further by reference to the accompanying drawings of which.

Figure 1:
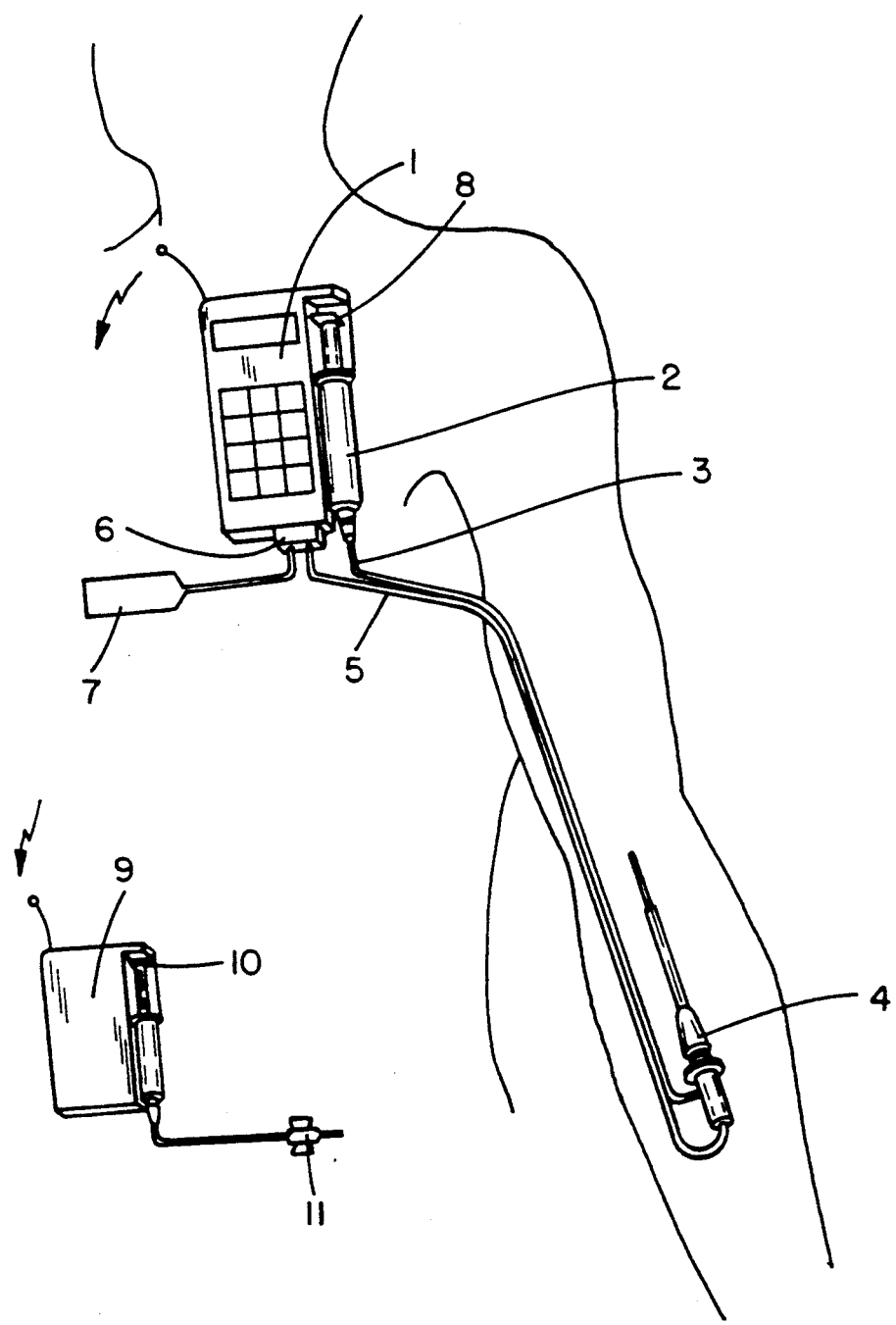
FIG. 1 is the overall apparatus, comprising the monitoring unit and the infusion device.
Figure 2:
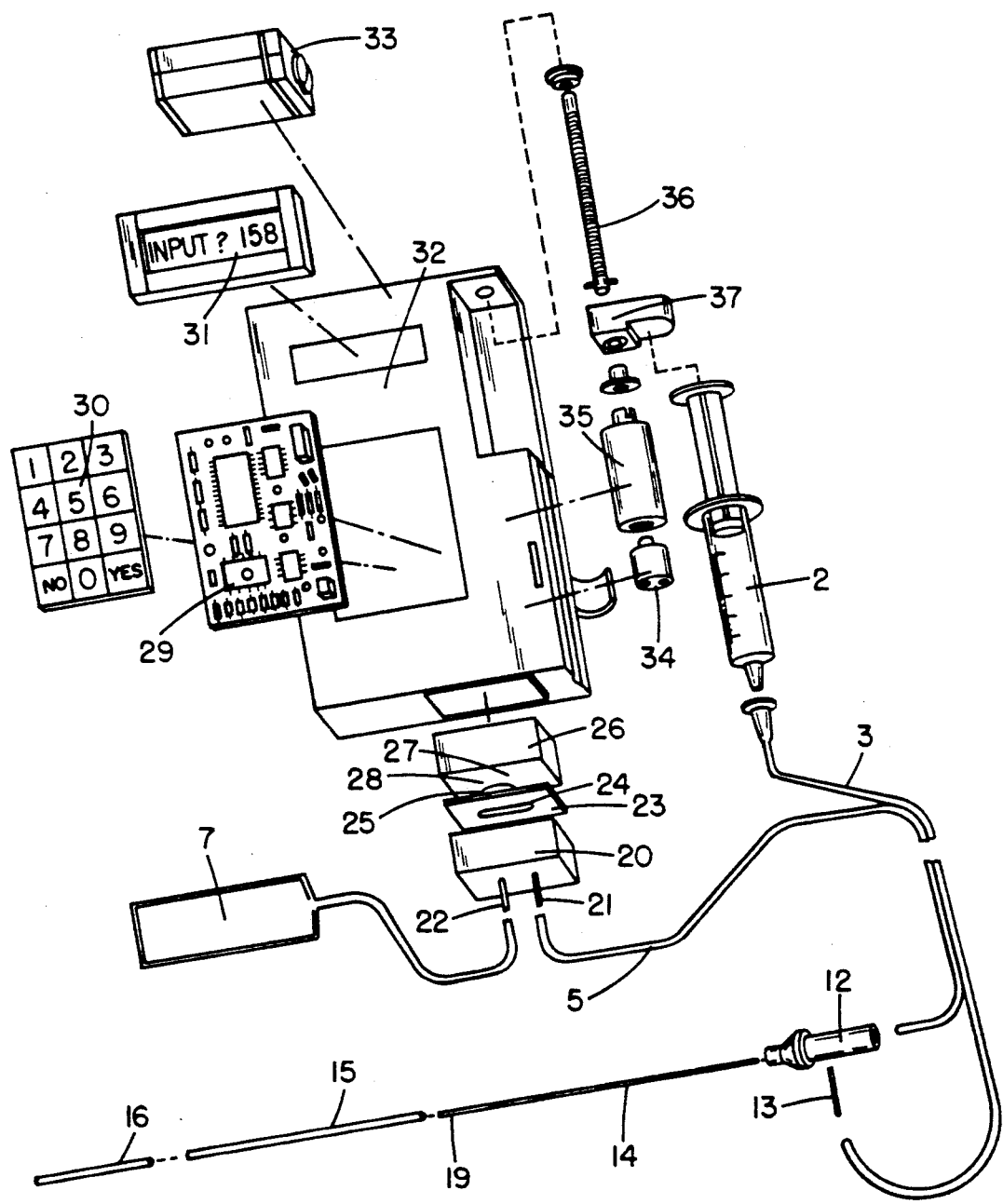
FIG. 2 is an exploded view of the apparatus used for measuring the glucose in the human body.
Figure 3:
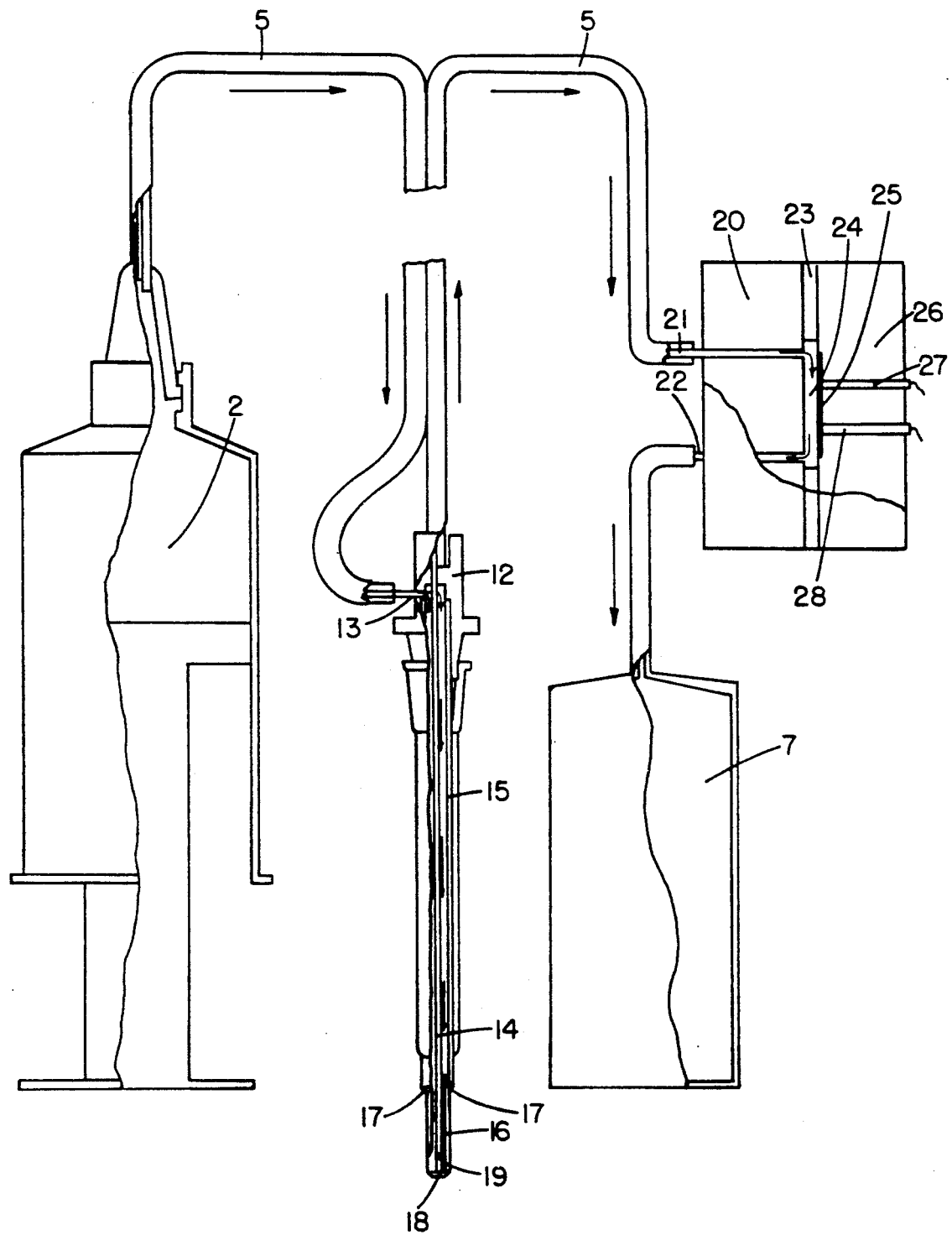
FIG. 3 is a diagram of the hydraulic system of the apparatus.
Figure 5:
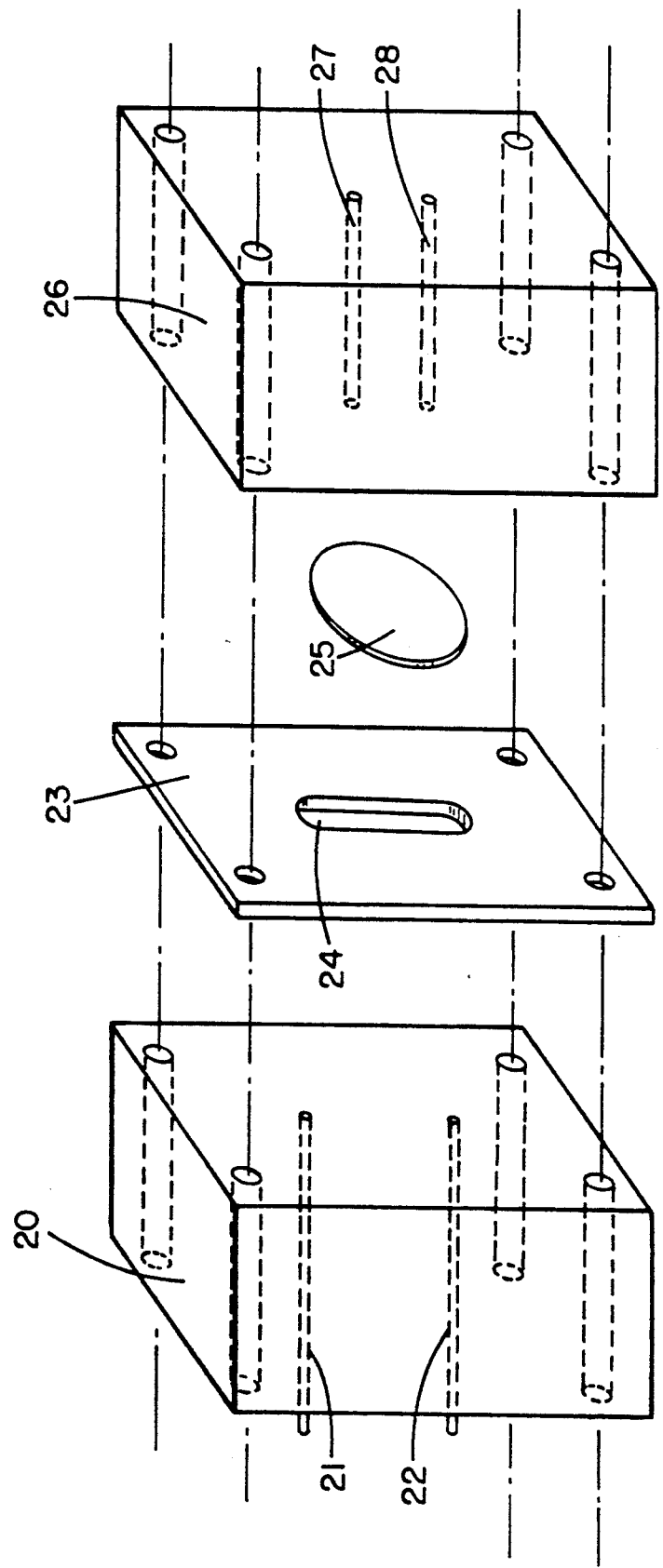
FIG. 5 is an exploded view of the measurement cell.
Figure 4:
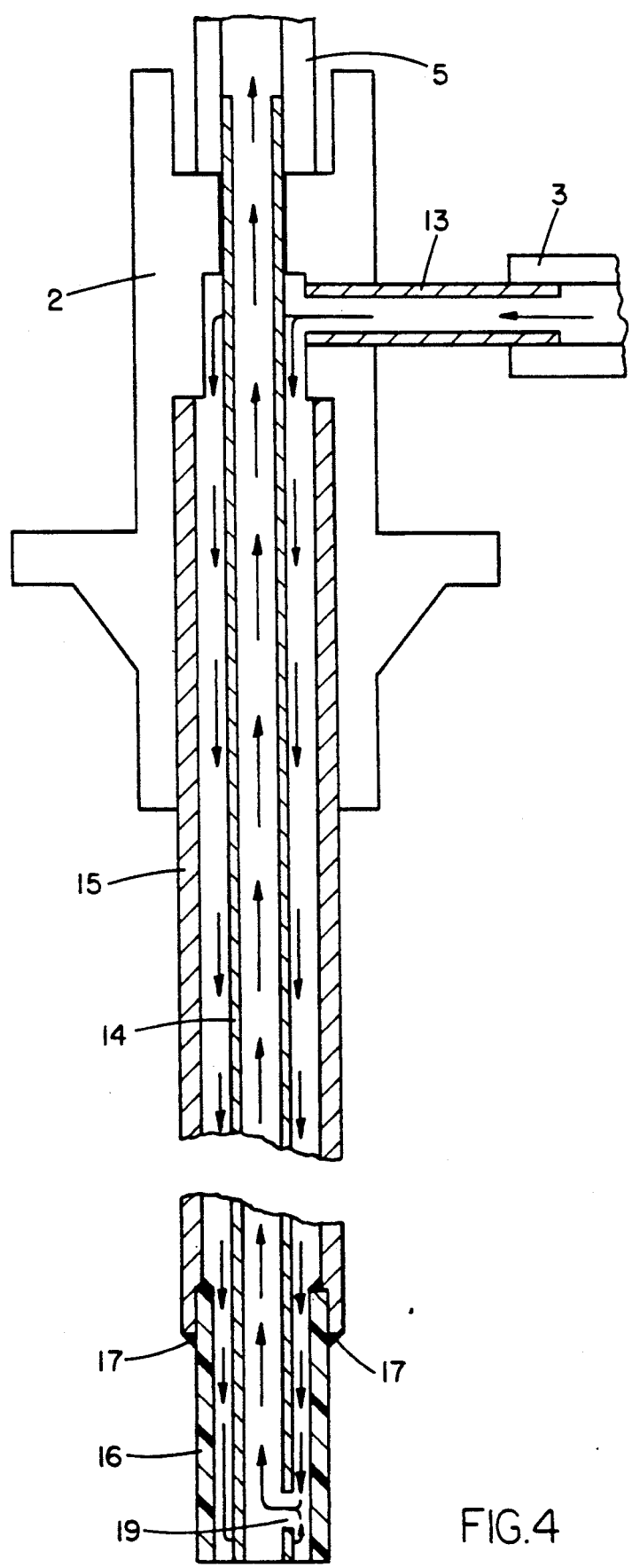
FIG. 4 is a cross section of the microdialyzing needle assembly.

The monitoring system designated by numeral 1 is the unit which continuously measures the blood glucose concentration.

By reference to the Figures, numeral 2 designates a syringe which contains saline solution, in the amount of about 6 ml, with heparin. Numeral 3 is the tube of plastic material, preferably Polyvinylcloride, of internal diameter 0.1-1 mm and about 50-80 cm in length which is connected with the microdialyzing needle 4.

A microdialyzing needle has been marketed only for the study of low molecular weight substances below 20,000 daltons on the cerebrospinal fluid or on the blood of small animals by Carnegie Medicine, Stockholm, Sweden, but, due to its dimensions and fragility, cannot be employed in humans.

The present invention utilizes the same physical principles of dialysis, but the needle here employed has dimensions, ruggedness and operativeness studied for use in human body.

The physical principles of dialysis state that the concentrations of substances contained in two solutions separated by a semipermeable membran have a tendency to become the same over a period of time because substances of low molecular weight tend to migrate from one side to the other of the membrane in order to reach equilibrium. The period of time required to reach equilibrium varies depending upon the physical properties of the semipermeable membrane and specifically the material used, the thickness, the size of the pores and upon the composition and concentration of the solutions, as well as their osmotic pressure.

One advantage of the method of the present invention resides in the fact that the microdialyzing needle is inserted in the interior of a vein and may remove a portion of the low molecular weight substances present in the blood without using any means for extracorporeal circulation. During the perfusion of the needle at low flux the chemical substances enter or leave the liquid of perfusion by diffusion through the semipermeable membrane which is present on the terminal part of the needle. Thus it is possible to diffuse the heparin present in the perfusion liquid in the space surrounding the needle in order to avoid the deposit of platelets and fibrin which could affect in a short period of time the physical properties of the dialyzing membrane, and, at the same time, it is possible to remove glucose and/or other metabolites being analyzed.

Again, by varying the flux of the perfusion solution, it is possible to change the ratio of the glucose diffused from the blood in order to obtain a proportional equilibrium. This is very useful since most of the enzymatic sensors used for the glucose assay have a range of linearity which is about 1/10 of the possible blood glucose range of a diabetic patient. By varying the flux of the perfusion solution it is possible to have a glucose concentration which is only 1/10 of the glycemic level.

Still another advantage according to the present invention is that by utilizing the microdialyzing needle, it is possible to maintain sterile conditions because the needle may be sterilized and the membrane protects the patient from the use of a perfusion liquid which may not be sterile. Further, the dimensions and the flow involved are extremely limited.

The assembly of the whole micro dialyzing needle is achieved by means of a plastic piece 12 to which three steel capillaries of different dimensions are fitted and glued. This plastic piece has the same external shape of the plastic hub of the stylet of the Ethicon Jellco 20 G vein catheter here used to place the micro dialyzing needle into the blood. All the dimensions of the steel capillaries given hereinbelow are referred to the use of the Ethicon Jellco 20G cannula. Other vein catheters could be used and the dimensions of the steel capillaries should be varied accordingly, in order to fit the internal diameter and the length of the catheter which is used. Once the Jellco catheter is inserted in the vein, the steel stylet is removed, and the microdialyzing needle is inserted into the teflon catheter in place of the stylet of the vein catheter. The plastic piece, shaped as the hub of the steel stylet, perfectly fits with the hub of the teflon cannula.

The perfusion liquid enters the needle through the steel capillary 13 of internal diameter 0.1-0.5 mm, external diameter of 0.2-1 mm and 5-15 mm. in length which is inserted in a hole placed at right angles to the axis of the microdialyzing needle.

The device comprises two steel capillaries assembled concentrically, the internal one 14 having an external diameter of 0.30 mm an internal diameter of 0.1 mm and a length of 79-85 mm., the external one 15 having external diameter of 0.72 mm., internal diameter of 0.40 mm. and a length of 61.5 mm. The internal diameter of the free end of the external capillary 15 is bored to a diameter of 0.50 mm. for a length of 1.5 mm.

A piece of Celanese Celgard X-20 400 um. hollow fiber of a length of 11.5-21.5 mm designated by the numeral 16 is inserted for the length of 1.5 mm into the boring of the internal diameter of the external steel capillary and there glued with the epoxy resin 17. It must be said that the Celgard X-20 hollow fiber membrane is satisfactory for this use, both for its dimensions and for its characteristics, but other materials could be used. Again the dimensions of the used membrane depend on the cannula and on the steel capillaries used. Some epoxy resin designated by numeral 18 is again used to close and glue together the two free ends of the hollow fiber 16 and of the internal steel capillary 14. The perfusion liquid flows into the space comprised between the hollow fiber 16 and the internal steel capillary 14. The equilibrium between the perfusion liquid which gives up heparin to the exterior and the blood from which glucose, lactic acid, and other substances of low molecular weight below 100,000 daltons (if Celgard X-20 is used) diffuse to the interior of the needle through the membrane, takes place in this area.

The perfusion liquid then enters into the lumen of the internal steel capillary 14 through an opening designated by numeral 19 which serves to place into connection the external numeral 19 which serves to place into connection the external space and the internal space of the capillary at a distance of 0.5-4 mm. from the glued end.

The perfusion liquid comes out from the microdialyzing needle through the tube 5 which is set on the internal steel capillary. Specifically, this is a tube of plastic material of about 50-80 cm. in length which carries the exiting liquid from the microdialyzing needle to the measurement cell. The internal diameter of this tube is extremely small, about 0.1-1 mm., for the purpose of reducing to a minimum the period of time required for the perfusion liquid to reach the sensor thus cutting down as much as possible the latent time prior to the measurement.

The glucose sensor 6 consists of a measuring flow cell coupled with an enzymatic membrane.

The measuring cell, which is a flow cell, consists of two blocks of plastic materials screwed together and separated by a thin plastic sheet. In the first block 20, there are two holes which are the input (21) and the output (22) of the liquid coming from the microdialyzing needle to and from the measurement cell.

The thin plastic sheet 23 has an ellyptic hole in the centre (24), and in the volume having for base the ellyptic hole area and for height the thickness of the sheet, the liquid coming from the microdialyzing needle flows coming in contact with the sensor. Thus is possible to obtain a very small flow chamber which is crossed very quickly by the liquid, so shorting the latent time to a minimum.

An enzymatic membrane containing glucose oxidase 25 is placed between the plastic sheet and the second plastic block 26 in which a Platinum (27) and a Silver wire (28) electrodes are threaded and glued.

The unit of the enzymatic membrane and of the platinum and silver wires constitute the glucose sensor used to measure the glucose concentration in the liquid coming from the microdialyzing needle. The sensor is an enzymatic amperometric one in which an enzymatic reaction is coupled with an amperometric electrode. As shown hereinbelow, the glucose oxidase (GOD) adherent to the membrane catalyzes the reaction:

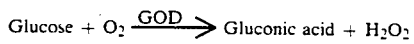

$$\text{Glucose} + O_2 \xrightarrow{\text{GOD}} \text{Gluconic acid} + H_2O_2$$

In this manner the glucose exiting from the microdialyzing needle is oxidized by the glucose oxidase contained in the membrane and is converted to gluconic acid with the production of hydrogen peroxide.

The hydrogen peroxide so produced diffuses and reaches the platinum-silver amperometric electrode. As explained above the electrode is constituted by the two silver and platinum wires threaded in the plastic block. The platinum is kept at a potential of about 650 mV with respect to the silver which serves as a reference. The potential favors the anodic dissociation of hydrogen peroxide according to the reaction:

$$H_2O_2 \rightarrow 2H^+ + O_2 + 2e$$

In this manner two electrons are set free for each molecule of oxidized glucose, and it is therefore possible to detect an electric current in the order of tens of nanoamperes between the platinum and the silver, a current which is proportional to the concentrations of glucose in the specimen being studied.

Numeral 7 is a reservoir of plastic material which is used to collect the liquid coming out from the measuring cell.

The electronic board 29 of the system controlled by a microprocessor, preferably made with Channel Metal Oxide Semiconductor (CMOS) technology for consumption reasons, and it is sufficient that it be an 8 bit in view of the number and the speed of the operations being performed, in this case from the family derived by Z80. The program for microprocessor functions is stored in an Erasable Programmable Read Only Memory (EPROM). By changing the program it is possible to adapt the instrument to a variety of sensors and to a variety of manners of operation. This may be necessary for concentration ranges different from the ones of blood glucose or for the conversion in different measuring units (mg<>mmol) used in foreign countries.

The microprocessor, on the basis of the program stored in the EPROM, controls the different functions carried out by the different actuators present in the monitoring unit, functions which will be described hereinbelow.

The glucose sensor 6 is polarized to about 650 mV with constant potential. A current to voltage converter simultaneously amplifies the current signal coming from the sensor to a level compatible with the input of a 10 bit analogic to digital converter which permits the microprocessor to acquire the same signal. In order to avoid that the measurements be affected by spurious disturbances which may accidentally occur, the signal is acquired and held every second by the microprocessor and the average of sixty values is calculated, and this average is considered the value of glycemia at that particular minute.

The microprocessor sends the data of the glycemia to the 8 Kbytes static CMOS Random Access Memory (RAM).

The microprocessors also commands the calibration procedures, necessary to let the sensor measures properly the glucose concentration, controlling the operations described hereinbelow. For the purpose of calibrating the measuring system, after filling the system with the perfusion solution and prior to inserting the microdialyzing needle in the patient, the current in the absence of glucose in the specimen is measured. This current is taken as the zero or base value. During the period of time when the apparatus is connected with the patient, the operator must determine the exact glycemic level of the individual by means of an external reference. After this evaluation the operator is requested to key in the level measured by the external reference and the electric current corresponding to that value is acquired by the microprocessor. After the current revealed by the sensor on contact with the two solutions, that is, the solution at glucose zero concentration and the value determined at the known concentration are measured, the equation which represents the linear regression between two points is calculated by the microprocessor, and this regression is used as a reference to determine the concentrations present in the specimen being studied, converting the measured currents.

The microprocessor controls every second the keyboard 30 present in the device for the purpose of verifying the input of data for the initial calibration and the eventual subsequent recalibrations. The same keyboard permits in addition to command the transmission of the glycemic data after the monitoring operation period has been completed.

Another function performed by the microprocessor is the transmission of the last minute data to the alphanumeric Liquid Cristal Display 31 for the purpose of showing to the operator the value as soon as it has been measured.

The every minute transmission of last measured glycemia is necessary order to carry out the blood glucose feedback control by means of an insulin infusion system. For this purpose an Amplitude Modulation trasmitter is used, the latter having a range of about 10 m. Data are being transmitted together with special codes in order to detect eventual transmission-reception errors.

At the end of the determination of the blood glucose profile, the operator may command the transmission of all every minute glycemias stored in the RAM to a personal computer so that a graphic representation of the profile can be obtained and the profile can be stored in a nonvolatile desired media.

There are also provided alarms to warn about software, measurement and hardware malfunctionings. A Light Emitting Diode and a buzzer call the attention of the operator or the patient to the fact that the instrument is not working properly.

The all monitoring system is contained in a plastic rugged box (32) which also provides a seat for the battery (33) which feeds the apparatus.

There is used a syringe pump 8 to provide for the advance of the perfusion solution through the apparatus. This pump comprises a micromotor 34 which through suitable gearings 35 causes a worm screw 36 to rotate, the latter carrying along a linear direction a small block made of plastic material 37 which in its turn pushes the piston of the syringe 2. A suitable seat facilitates the positioning of the syringe on the pump.

The infusion system 9 used in the present invention constitutes a substantial advance with respect to the infusion systems known in the art. In order to increase the flexibility of the apparatus, there is used an infusion unit programmable by a personal computer with the resolution of one minute so that the infusion profile may be obtained at a different rate from minute to minute with absolute accuracy according to the necessity of administration for different individuals. Further, the infusion system receives the data transmitted by the monitoring unit and by means of a suitable algorithm memorized in the interior of the electronic system calculates the quantity of insulin to be administered to the patient for the purpose of reaching and maintaining the predetermined desired glycemic level. This algorithm is derived by the analysis of the two characteristic behaviors of the insulin secretion in response to the amount of glucose in the blood, the first behaviors being dependent on the actual level of glycemia, and proportional to it, and the second behaviors depending on the rate of variation, increase or decrease of the concentrations of glucose in the blood. The first behaviors is called "static control", while the second one is called "dynamic control". By using an algorithm which imitates the combination of the two behaviors, the infusion system responds very close to the actual functioning of the beta pancreatic cells and administers to the patient the proper quantity of insulin calculated every minute on the basis of the glycemic values received from the monitoring unit. The infusion profiles so calculated may be memorized in the interior of the system thus permitting the use as an insulin pump preprogrammed on the basis of the real necessity of the patient calculated with the monitoring unit without using the latter.

A syringe pump 10 similar to the one of the monitoring unit is used to push the insulin into the needle 11 inserted in the patient examined.

What is claimed is:

1. A device for the continuous quantitative determination of glucose in the blood of a diabetic patient over a period of 24-36 hours, which comprises a container for a saline solution containing heparin, a microdialyzing needle inserted into a vein of said diabetic patient, pumping means for injecting said solution through said microdialyzing needle which contains a semipermeable plastic hollow fiber membrane located on its outer surface whereby dialysis occurs between the blood in the vein and said solution and only glucose and other substances of low molecular weight below 100,000 daltons go through said semipermeable fiber membrane and the concentration of said glucose and other substances of low molecular weight below 100,000 daltons reaches an equilibrium which is proportional to the actual concentration of glucose in the blood, and a glucose-containing saline solution is obtained, said microdialyzing needle being provided with an outgoing conduit, said conduit leading to a sensor, said sensor comprising a platinum silver electrode and an enzymatic membrane containing glucose oxidase, said glucose containing saline solution goes into said conduit, oxidation of glucose to gluconic acid and hydrogen peroxide occurs and said hydrogen peroxide is decomposed with the liberation of two electrons whereby electric current is produced, the concentration of glucose in the blood is determined by determining the amount of current produced, without recirculation of blood, said glucose containing saline solution contains about 1/10 of the glucose concentration in the blood and said saline solution is discarded.

2. The device according to claim 1 which is capable of transmitting the data of the blood glucose concentration of a diabetic patient over a period of 24-36 hours to a computer.

3. A device for the continuous quantitative analysis of glucose in the blood of a diabetic patient over a period of 24-36 hours and for the injection of insulin and/or glucose into said patient depending upon the results of said analysis which comprises the device according to claim 1, and means for the injection of insulin and/or glucose at one minute intervals.

4. The device according to claim 1 wherein in said microdialyzing needle one internal capillary and one external capillary are located, said saline solution flows therebetween, said hollow fiber membrane is located at the terminal part of said needle and the saline solution flows between said internal capillary and said hollow fiber membrane.

5. The device according to claim 4 wherein said internal capillary has an opening at the terminal end thereof to connect with the external capillary.

6. A device for the short term continuous quantitative determination of lactate in the blood of an athlete or of a heart patient, which comprises a container for a saline solution containing heparin, a microdialyzing needle inserted into a vein of said athlete or heart patient, pumping means for injecting said solution through said microdialyzing needle which contains a semipermeable plastic hollow fiber membrane located on its outer surface whereby dialysis occurs between the blood in the vein and said solution and only lactate and other substances of low molecular weight below 100,000 daltons go through said semipermeable fiber membrane and the concentration of said lactate and other substances of low molecular weight below 100,000 daltons reaches an equilibrium which is proportional to the actual concentration of lactate in the blood, and a lactate containing saline solution is obtained, said microdialyzing needle being provided with an outgoing conduit, said conduit leading to a sensor, said sensor comprising a platinum silver electrode and an enzymatic membrane containing lactate oxidase, said lactate containing saline solution goes into said conduit, oxidation of lactate to pyruvate and hydrogen peroxide occurs and said hydrogen peroxide is decomposed with the liberation of two electrons whereby electric current is produced, and the concentration of lactate in the blood is determined by determining the amount of current produced without recirculation of blood, said lactate containing saline solution contains about 1/10 of the lactate concentration in the blood, and said saline solution is discarded.

7. The device according to claim 6 wherein in said microdialyzing needle one internal capillary and one external capillary are located, said saline solution flows therebetween, said hollow fiber membrane is located at the terminal part of said needle and the saline solution flows between said internal capillary and said hollow fiber membrane.

8. The device according to claim 6 wherein in said microdialyzing needle one internal capillary and one external capillary are located, said saline solution flows therebetween said hollow fiber membrane is located at the terminal part of said needle said internal capillary has an opening at the terminal end thereof to connect with the external capillary.

* * * * *